United States Patent [19]

Kitajima et al.

[11] Patent Number: 5,460,777
[45] Date of Patent: Oct. 24, 1995

[54] ANALYTICAL ELEMENT FOR WHOLE BLOOD ANALYSIS

[75] Inventors: Masao Kitajima; Masashi Ogawa; Osamu Seshimoto, all of Saitama, Japan

[73] Assignee: Fuji Photo Film Co., Ltd., Kanagawa, Japan

[21] Appl. No.: 29,799

[22] Filed: Mar. 11, 1993

[30] Foreign Application Priority Data

Mar. 16, 1992 [JP] Japan .................................. 4-058486
Feb. 19, 1993 [JP] Japan .................................. 5-30255

[51] Int. Cl.⁶ .................................................. G01N 33/49
[52] U.S. Cl. ........................... 422/56; 422/58; 436/170
[58] Field of Search ............................ 422/56, 57, 58; 436/169, 170

[56] References Cited

U.S. PATENT DOCUMENTS 5,118,472  6/1992  Tanaka et al. .............................. 422/56
5,135,716  8/1992  Thakore .................................... 422/56
5,256,372  10/1993  Brooks et al. ............................ 422/58

*Primary Examiner*—Lyle A. Alexander
*Attorney, Agent, or Firm*—McAulay Fisher Nissen Goldberg & Kiel

[57] ABSTRACT

An analytical element for whole blood which comprises a blood cell-separating layer having a volume smaller than the upper limit of the diffused volume of a whole blood sample having a hematocrit value of 70% provided on a porous layer, and a method of measuring an analyte which comprises spotting a whole blood sample onto the above analytical element removing the blood cell-separating layer after blood plasma portion of the sample is diffused into the porous layer, supplying a fixed amount of measuring reagent solution having a diffused area smaller than the diffused area of the blood plasma to measure the analyte. According to the invention, the analytical error caused by scattering of hematocrit values is removed, and analysis can be conducted in a high accuracy.

9 Claims, 1 Drawing Sheet

FIG. 1

ANALYTICAL ELEMENT FOR WHOLE BLOOD ANALYSIS

BACKGROUND OF THE INVENTION

This invention relates to a dry analytical element capable of analyzing whole blood sample.

Recently, biochemical assay of blood has been frequently conducted, and dry analytical elements tend to be used for the biochemical assay.

In the past, the sample to be analyzed was usually blood serum or blood plasma where the erythrocytes were removed, irrespective of whether the wet or dry method was used. However, since the separation of erythrocytes requires labor and equipment cost, analysis is preferably carried out using undiluted whole blood.

When whole blood is analyzed by the dry method, blood cells, i.e. erythrocytes and leukocytes, and other solid components should be separated in the analytical element by some means. A means therefor is to provide a blood cell-separating layer in a multilayer anlaytical element. Japanese Patent KOKAI Nos. 57-53661 and 61-96466 disclose that glass fiber, membrane filter, cottom fiber, wool fiber and the like can be used for the blood cell-separating layer. It is also known to combine two or more layers, and Japanese Patent KOKAI Nos. 62-138756 and 3-16651 disclose to combine a fibrous porous layer and a nonfibrous porous layer.

The blood cell components of whole blood is great ranging over 70% as hematocrit value. Accordingly, permeation and diffusion of plasma portion were liable to be uneven due to the occurrence of clogging in the blood cell-separating layer. As a result, there was a problem that analytical results varied according to the measured portion in the analytical element resulting to induced errors. Besides, it was also a great problem that the analytical errors caused by scattering of the spotted amounts of whole blood sample and scattering of hematocrit values. Moreover, since whole blood samples have a high viscosity, it is difficult to take a very small amount and to spot it accurately. Therefore, it is very difficult to put a simple blood analytical element to practical use without a means to decrease the above liquid amount errors.

SUMMARY OF THE INVENTION

An object of the invention is to provide an analytical element for whole blood which prevents uneven permeation and diffusion during separating blood cells by a simple means and resolves the scattering of spotted amounts and hematocrit values of whole blood samples and the analytical error caused by the difference in the spotted liquid amounts.

The present invention provides an analytical element for whole blood which has achieved the above object, and comprises a blood cell-separating layer having a volume smaller than the upper limit of the diffused volume of a whole blood sample having a hematocrit value of 70% provided on a porous layer.

The present invention also provides a method of measuring an analyte which comprises spotting a whole blood sample onto the above analytical element, removing the blood cell-separating layer after blood plasma portion of the sample is diffused into the porous layer, supplying a fixed amount of measuring reagent solution having a diffused area smaller than the diffused area of the blood plasma to measure the analyte.

DETAILED DESCRIPTION OF THE INVENTION

The blood cell-separating layers applicable to the invention include integrated ones of a fibrous porous layer with a nonfibrous porous layer joined by partially disposed adhesive (partial adhesion) disclosed in Japanese Patent KOKAI Nos. 62-138756-8, 2-105043, 3-16651, etc., microporous layers having blood cell-separating ability, such as made of fluorine-containing polymer or polysulfone of which the surface is rendered hydrophilic. Particularly preferred blood cell-separatig layers are formed of a fibrous porous layer disposed on the spotting side of blood and a nonfibrous porous layer disposed on the layer to receive the plasma portion of the analytical element portion joined to each other by the partial adhesion described later.

Preferable nonfibrous porous layers, in the above blood cell-separating layer composed of a fibrous porous layer and a nonfibrous porous layer joined by partial adhesion, are blushed polymer layers composed of a cellulose ester, such as cellulose acetate, cellulose acetate/butyrate or cellulose nitrate, disclosed in U.S. Pat. Nos. 3,992,158 or 1,421,341. The nonfibrous porous layer may be a microporous membrane of polyamide, such as 6-nylon or 6,6-nylon, or polyethylene, polypropylene, or the like. Other nonfibrous porous layers usable for the blood cell-separating layer include continuous microspace-containing porous layers where polymer particulates, glass particulates, diatomaceous earth or the like are joined by a hydrophilic or non-water-absorptive polymer, such as disclosed in U.S. Pat. No. 3,992,158, and 4,258,001.

Preferable effective pore size of the nonfibrous porous layer is 0.3 to 30 μm, and 0.5 to 5 μm is particularly preferred. The effective pore size of the nonfibrous porous layer in the invention is the pore size measured by the bubble point method according to ASTM F316-70. In the case that the nonfibrous porous layer is a membrane filter composed of blushed polymer prepared by the phase separation method, the liquid passages in the thickness direction are, in general, the narrowest at the free surface (glossy face) in the manufacturing process of the membrane, and the pore size in section of each liquid passage stipulated a circle is the smallest near the free surface. The minimum pore size of passages in the thickness direction per unit area has a distribution in facial direction of the membrane filter, and the maximum value determines filtration performance. In general, it is determined by the limit bubble point method.

As mentioned above, in the membrane filter composed of blushed polymer prepared by the phase separation method, liquid passages in the thickness direction become the narrowest at the free surface (glossy face) in the manufacturing process of the membrane. In the case of using the membrane as the nonfibrous porous layer of the analytical element of the invention, it is preferable to face the glossy face of the membrane filter toward the analytical element portion to receive the plasma portion.

The material composing the fibrous porous layer may be filter paper, nonwoven fabric, woven fabric such as plain weave fabric, knitted fabric such as tricot fabric, glass fiber filter paper, etc. Among them, woven fabric and knitted fabric are preferred. The woven fabric or the like may be treated by glow discharge as disclosed in Japanese Patent KOKAI No. 57-66359.

Since the fibrous porous layer is utilized as the spreading layer of liquid sample, it is preferable to have a liquid metering function. The liquid metering fuction is to spread components contained in an aqueous liquid sample spotted on its surface in plane at a rate of a constant quantity per unit area without uneven distribution. The spreading layer may contain a hydrophilic polymer or a surfactant in order to control spreading area, spreading speed and the like as disclosed in Japanese Patent KOKAI Nos. 60-222770, 63-219397, 63-112999, 62-182652.

The void volume (per unit area) of the fibrous porous layer may be equal to or different from the nonfibrous porous layer. The void volume correlation between them may be adjusted by changing either or both of void content and thickness.

The microporous layer having blood cell-separating ability of which the surface is rendered hydrophilic separates the blood cells and the plasma from whole blood specifically without hemolysis to the degree substantially not affecting the analytical values.

Althouth the blood cell-blood plasma separation mechanism is not clear, it is thought that the microporous layer does not trap blood cells only by the surface, but catches to remove blood cells gradually by entangling at first large blood cell components and then smaller blood cell components in the space structure with permeating in the thickness direction in total of the microporous layer composed of fluorine-containing polymer and the porous spreading layer, called the volumetric filtration.

As the fluorine-containing polymer sheets usable as the microporous layer, there are the microporous matrix layer (microporous layer) composed of polytetrafluoroethylene fibrils (fines) disclosed in WO 87/02267, Gore-Tex (W. L. Gore and Associates), Zitex (Norton), Poreflon (Sumitomo Denki), etc. Other fluorine-containing polymer sheets usable as the microporous layer include polytetrafluoroethylene microporous membranes disclosed in U.S. Pat. Nos. 3,368,872 (Examples 3 and 4), 3,260,413 (Examples 3 and 4), 4,201,548, etc., polyvinylidenefluoride microporous membranes disclosed in U.S. Pat. No. 3,649,505 and the like. Among the above fluorine-containing polymer microporous membranes, particularly suitable membranes for the microporous layer constructing the blood cell filtering layer are those having a small pore size which substantially does not pass red blood cells, a thin thickness and a great void content. Actually, preferred membranes have a pore size of about 0.2 to 60 µm, preferably about 1 to 20 µm, more preferably about 1 to 10 µm, a void content of about 40 to 95%, preferably about 50 to 95%, more preferably about 70 to 95%, and a thickness of about 10 to 200 µm, preferably about 30 to 150 µm, in view of handling in the manufacturing process, such as the occurrence of wrinkling, the most preferably about 50 to 120 µm. The microporous membrane of fluorine-containing polymer may be prepared by using a single fluorine-containing polymer or blending two or more kinds of fluorine-containing polymers or further blending one or more polymers not containing fluorine or fibers therewith. As the structure, there are unstretched one, uniaxially stretched one, biaxially stretched one, nonlaminated single layer type, laminated double layer type, such as a membrane laminated to another membrane structure such as a fiber membrane. In the case of nonlaminated type microporous membrane having fibril structure or having been uniaxially or biaxially stretched, microporous membrane having a great void content and a short filtering pass can be prepared by stretching. In microporous membranes having a short filtering pass, clogging rarely occurs by solid components (mainly red blood cells) in blood, and the separation time of blood cells and plasma is short. As a result, accuracy in quantitative analysis is improved. The adhesive strength of adhesive used for the partial adhesion to the adjacent porous layer can be strengthened by providing the physical activation (preferably glow discharge or corona discharge) disclosed in U.S. Pat. No. 4,783,315 on at least one side of the microporous layer of fluorine-containing polymer to render hydrophilic.

It is wellknown that fluorine-containing polymer microporous membranes as it is have a low surface tension. As a result, when the membrane is used as the blood cell filtering layer, aqueous liquid samples are repelled and do not diffuse nor permeate over the surface or into the inside. In the analytical element of the invention, the above repelling problem has been resolved by incorporating a sufficient amount of surfactant for rendering the outer surface and the inner space surface of the fluorine-containing polymer microporous membrane substantially hydrophilic thereinto. In order to impart a hydrophilic property sufficient for diffusing, permeating or moving an aqueous liquid sample over the surface or into the inside of the fluorine-containing polymer microporous membrane without repelling to the membrane, in general, it is necessary that the space surface of the membrane is coated with a surfactant in an amount of about 0.01 to 10%, preferably about 0.1 to 5%, more preferably about 0.1 to 1% of the void volume of the membrane. For example, in the case of a fluorine-containing polymer microporous membrane 50 µm in thickness, a preferred amount of surfactant to be impregnated is usually in the range of 0.05–2.5 g/m². As the method of impregnating surfactant into a fluorine-containing microporous membrane, a common method comprises immersing the fluorine-containing microporous membrane in the surfactant solution dissolved in a low boiling point (a preferable boiling point is in the range of about 50° C. to about 120° C.) organic solvent (e.g. alcohols, esters, ketones) to permeate into the inner spaces of the membrane substantially sufficiently, taking the membrane out of the solution slowly, and then drying by blowing air (preferably warm air). The surfactant may be incorporated into the fluorine-containing polymer microporous membrane together with other components such as pretreatment reagents for the microporous membrane constructing a blood cell filtering layer.

As the surfactant for rendering the fluorine-containing polymer microporous membrane hydrophilic, the surfactant may be nonionic, anionic, cationic or ampholytic. However, nonionic surfactants are advantageous for the multilayer analytical elements for analyzing whole blood samples, because nonionic surfactants have a relatively low hemolytic activity among the above surfactants. Suitable nonionic surfactants include alkylphenoxypolyethoxyethanol, aklylpolyether alcohol, polyethyleneglycol monoester, polyethyleneglycol diester, higher alcohol-ethylene oxide adduct (condensate), polyol ester-ethylene oxide adduct (condensate), higher fatty acid alkanol amide, etc. Examples of the nonionic surfactant are as follows: As the alkylphenoxypolyethoxyethanol, there are isooctylphenoxypolyethoxyethanols (Triton X-100; containing 9–10 hydroxyethylene units on average, Triton X-45; containing 5 hydroxyethylene units on average) and nonylphenoxypolyethoxyethanols (IGEPAL CO-630; containing 9 hydroxyethylene units on average, IGEPAL CO-710; containing 10–11 hydroxyethylene units on average, LENEX 698; containing 9 hydroxyethylene units on average). As the alkylpolyether alcohol, there are higher alcohol polyoxyethylene ethers (Triton X-67; CA Registry No. 59030-15-8), etc.

The fluorine-containing polymer microporous membrane may be rendered hydrophilic by providing one or more water-insolubilized water-soluble polymers in its porous spaces. The water-soluble polymers include oxygen-containing hydro carbons, such as polyvinyl alcohol, polyethylene oxide, polyethylene glycol, methyl cellulose, ethyl cellulose, hydroxyethyl cellulose and hydroxypropyl cellulose, nitrogen-containing ones, such as polyacrylamide, polyvinylpyrrolidone, polyvinylamine and polyethylenemine, negative charge-containing ones, such as polyacrylic acid, polymetacrylic acid and polystyrene sulfonic acid, and the like. The water-insolubilization may be conducted by heat treatment, acetal-inducing treatment, esterification, chemical reaction by potassium dichromate, crosslinking by ionizable radiation, or the like. Details are disclosed in Japanese Patent KOKOKU Nos. 56-2094 and 56-16187.

The polysulfone microporous membrane can be prepared by dissolving polysulfone into dioxane, tetrahydrofuran, dimethylformamide, dimethylacetamide, N-methyl-2-pyrrolidone or a mixed solvent thereof to obtain a raw liquid for forming film, casting into film by flowing directly into a coagulating solution, washing, and then drying. Details are disclosed in Japanese Patent KOKAI No. 62-27006. In addition, polysulfone microporous membranes are also disclosed in Japanese Patent KOKAI Nos. 56-12640, 56-86941, 56-154051, etc., and they are applicable to the invention. The polysulfone microporous membrane can be rendered hydrophilic, similar to the fluorine-containing polymer, by incorporating surfactant or providing water-insolubilized water-soluble polymer.

The volume of the blood cell-separating layer is rendered smaller than the upper limit of the diffused volume of a whole blood sample having a hematocrit value of 70%. The upper limit of the diffused volume means the diffusion-permeation limit in planar directions, when the area of the blood cell-separating layer is made sufficiently great and the whole blood sample is freely spread. The value varies according to the material, construction and the like of the blood cell-separating layer, even when the same whole blood sample is used. When the blood cell-separating layer is composed of two or more layers, the volume is the total of the volumes of each layer. When a whole blood sample is spotted onto the blood cell-separating layer, blood cell portion remains at the center, and plasma portion is diffused over the circumference. The upper limit of the diffused volume means the maximum diffused range of the plasma portion. The maximum diffused range is greatly influenced by the spotted amount of a whole blood sample and hematocrit value thereof. In the invention, the upper limit of the diffused volume is determined by spotting a whole blood sample having a hematocrit value of 70% which is almost the greatest hematocrit value among whole blood samples in an amount of the lower limit of scattering of spotted amounts, actually, the spotted amount of 95% of the samples becoming greater than that, and leaving at room temperature at 50% in relative humidity for 2 minutes to determine the diffused range. The above test is repeated as to a plurality of, usually about ten, whole blood samples, and the mean value of the diffused range is used as the maximum diffused range. The upper limit of the diffused volume is determined by multiplying the thickness of the blood cell-separating layer by the maximum diffused range. The volume of the blood cell-separating layer is rendered smaller than the upper limit of the diffused volume, preferably about 40 to 95%, more preferably about 50 to 85%, and the most preferably about 60° to 80° C. of the upper limit of the diffused volume. Actually, the spotted amount of whole blood sample is selected from the range of about 15 to 50 μl, preferably about 20 to 45 μl, and the most preferably about 25 to 40 μl.

The porous layer is the layer to receive the plasma portion diffused from the blood cell-separating layer, and known spreading layers for multilayer analytical element can be used as the porous layer.

The spreading layer has a function to spread components contained in an aqueous liquid sample in plane without uneven distribution and to supply them to the hydrophilic polymer layer at a constant rate per a unit area, and may be composed of every nonfibrous or fibrous porous material known for the spreading layer of conventional dry analytical elements. Examples of the spreading layer include nonporous isotropic microporous medium layers represented by membrane filter (blushed polymer) disclosed in U.S. Pat. No. 3,992,158, nonfibrous porous layers represented by continuous space-containing three dimensional lattice grain structure layer where polymer particulates are joined at spots by a water-nonswelling adhesive disclosed in U.S. Pat. No. 4,258,001, porous layers composed of woven fabric disclosed in U.S. Pat. No. 4,292,272, GB 2,087,074A, etc., porous layers composed of knitted fabric disclosed in EP 0,162,302A, various filter papers, hydrophilic papers and the like.

The spreading layer may be composed of two or more microporous layers as disclsed in EP 0,166,365A, EP 0,226, 465A, etc. As to the multilayer anlaytical element wherein two or more spreading layers are superposed, it is necessary to have the construction that all layers are integrally laminated at the time of sample spotting, but it is not necessary to be integrated in the subsequent processes. Optionally, the analytical element can be used in the state that the first spreading layer is separated from the second spreading layer.

The spreading layer may contain a nonionic, anionic, cationic or ampholytic surfactant in order to accelerate spreading of a sample. Besides, it may contain a spreading controller, such as hydrophilic polymer for the purpose of controlling spreading. Furthermore, it may contain all or a part of various reagents for accelerating the object detecting reaction or reducing or inhibiting interfering reactions.

A suitable thickness of the spreading layer is 20 to 200 μm, preferably 50 to 170 μm, more preferably 80 to 150 μm.

The interface between the porous layer and the blood cell-separating layer is sufficient so as to diffuse and permeates therebetween, and the porous layer may be joined or not joined to the blood cell-separating layer. In the case of joining, they are joined by the following partial adhesion so as not to interfere the diffusion or permeation of the plasma portion. The partial adhesion is a form of adhesion between 2 porous layers or a porous layer and a nonporous layer adjacent to each other disclosed in EP 0,166,365 A, EP 0,226,465 A, etc., and it is an adhesion where 2 adjacent layers are substantially closely joined and integrated by adhesive disposed partially or intermittently at their interface and arranged so that uniform passage of liquid is substantially not inhibited at the 2 faces adjacent to each other and the space therebetween.

As the method of disposing adhesive partially onto the blood cell-separating layer or the porous layer, it may be conducted according to the method disclosed in Japanese Patent KOKAI Nos. 61-4959, 62-138, 756, DE 3,721,236 A, etc. Among the above various methods, the printing method is preferred. In the printing method, the process of transferring to adhere adhesive to a porous layer or a detecting function layer using a printing plate roller (gravure printing plate or intaglio printing plate is preferred) and the process of joining adjacent two layers can be conducted, for example, by using a knwon apparatus and method disclosed in Ed. Japan Printing Society, "Insatsu Kogaku Binran (Printing Engineering Handbook)", pp 839–853, Gihodo Shuppan, Tokyo, 1983, etc.

The adhesives applicable are disclosed in Japanese Patent KOKAI No. 62-138756, the above "Insatsu Kogaku Binran", pp 839–853, etc. The adhesive may be in water solvent type, organic solvent type or themal adhesion (or heat-sensitive) type. As the water solvent type adhesive, there are aqueous pastes, such as starch paste, aqueous solutions of dextrin, carboxymethyl cellulose, polyvinyl alcohol, etc., and vinyl acetate-butyl acrylate copolymer emulsion. As the organic solvent type adhesive, those having a slow evaporation speed of the solvent are suitable. Thermal adhesion (or heat-sensitive) type adhesives are particularly useful. As the hot-melt type adhesives in thermal adhesive (or heat-sensitive) type, the hot-melt type adhesives disclosed in "Kogyo Zairyo (Industrial Materials)", vol. 26 (No. 11), pp 4–5 are usable. Examples are ethylene copolymers, such as ethylene-vinyl acetate copolymer, ethylene-ethyl acrylate copolymer and ethylene-acrylic acid copolymer, polyolefins, such as low molecular weight polyethylene or atactic polypropylene, polyamides, such as nylon, thermoplastic rubbers, such as SBS and other styrene block copolymers, styrene-butadiene rubber, butyl rubber, urethane rubber, rosin, petroleum resin, terpere resin, and synthetic wax. Among them, silicone group, acrylic group and phenol group pressure-sensitive adhesives are particularly useful for the invention.

In the analytical element for whole blood, in general, at least one layer of hydrophilic polymer layers is laminated onto the water-impermeable support.

The hydrophilic polymer layer may be composed of various known polymers which are water-soluble, swellable and hydrophilic and are used for conventional dry analytical-elements. The hydrophilic polymer is generally a natural or synthetic hydrophilic polymer having a swelling ratio in the range of about 1.5 to about 20 times preferably from about 2.5 to about 15 times at water absorption at 30° C. Examples of the hydrophilic polymer are gelatines, such as acid-treated gelatin and deionized gelatin, gelatin derivatives, such as phthalated gelatin and hydroxyacrylate-graft gelatin, agarose, pullulan, pullulan derivatives, polyacrylamide, polyvinyl alcohol and polyvinylpyrrolidone. Instead of the hydrophilic polymer layer, paper or porous polymer membrane having hydrophilic surface can be used.

A suitable thickness of the hydrophilic polymer layer is about 1 to 100 μm, preferably about 3 to 50 μm, more preferably about 5 to 30 μm. It is preferred that the hydrophilic layer is substantially transparent. The hydrophilic polymer layer may contain all or a part of various reagents for accelerating the object detecting reaction or reducing or inhibiting interfering reactions.

The water-impermeable support may be a known water-impermeable support used in conventional dry analytical elements, and includes a transparent film made of polyethylene terephthalate, polycarbonate of bisphenol A, polystyrene, cellulose ester, such as, cellulose diacetate, cellulose triacetate or cellulose acetate propionate, or the like. The thickness of the support is usually in the range of about 50 μm to about 1 mm, preferably from about 80 μm to about 300 μm. The support is usually light-transmissive, but in the case of measuring from the spreading layer side, it may be colored or may be opaque. The support may be provided with an undercoating layer on its surface in order to strengthen the adhesion of the hydrophilic polymer layer.

In the method of the invention, the analyte to be measured is not limited, and any analyte usually measured in clinical assay field of which the analytical method has already established can be measured, such as enzymes, lipids, inorganic ions, metabolites, proteins, various components derived from living body, such as globulins, antigens and antibodies, medicines, hormones and tumor markers.

The analytical element for whole blood used in the invention may have various constructions described below according to the analytical item or the sample to be measured.

1. Analytical element having a layer construction of water-impermeable suport/hydrophilic polymer layer/spreading layer/blood cell-separating layer, and not containing a reagent directly reacting with analyte to produce chemical change:

This analytical element is effective for the analysis of Ca, GOT (glutamic-oxaloacetic transaminase), GPT (glutamic-pyruvic transaminase), γ-GTP (γ-glutamyl transpeptidase), glucose, LDH (lactate dehydrogenase), CPK (creatine phosphokinase), TP (total protein), Alb (albumin), Tcho (total cholesterol), UA (uric acid), neutral fats, etc.

2. Analytical element having a layer construction of water-impermeable support/hydrophilic polymer layer/spreading layer/blood cell-separaing layer, containing chromogen in the hydrophilic polymer layer and/or the spreading layer, but not containing a reagent directly reacting with analyte to produce chemical change:

The chromogen applicable to the invention includes 4-aminoantipyrines (synonym: 4-aminophenazone, i.e. 1-phenyl-2,3-dimethyl-4-amino-3-pyrazoline-5-one) disclosed in Ann, Clin. Biochem., 6, 24–27 (1969), and 4-aminoantipyrine analogs, such as tri-substituted-4-amino-3-pyrazoline-5-one such as 1-(2,4,6-trichlorophenyl)-2,3-dimethyl-4-amino-3- pyrazoline- 5-one and 1-(3,5-dichloropheynyl)-2,3-dimethyl-4-amino- 3-pyrazoline-5-one disclosed in EP 0,103,901A, and 1-phenyl-2,3-dimethyl-4-dimethylamino-3-pyrazoline-5-one disclosed in U.S. Pat. No. 3,886,045. Preferred compounds are 4-aminoantipyrine, 1-(2,4,6-trichlorophenyl)-2,3-dimethyl-4-amino- 3-pyrazoline-5-one, 1-(3,5-dichlorophenyl)-2,3-dimethyl- 4-amino-3-pyrazoline-5-one, and the like.

3. Analytical element having a layer construction of water-impermeable support/hydrophilic polymer layer/spreading layer/blood cell-separating layer and containing chromogen and other reagents (excluding the measuring reagent described later) in hydrophilic polymer layer and/or spreading layer:

Examples of the other reagents are POP (peroxidase), NAD (nicotinamide adenine dinucleotide), NADP (nicotinamide adenine dinucleotide phosphate), DIP (diaphorase), etc.

In the above constructions of 2 and 3, the chromogen and the other reagents can be supplied after a liquid sample is supplied and then stabilized. This is preferable, because most of the chromogens are water-insoluble and therefore it is necessary to add separately. Better reproducibility can be obtained by preparing the analytical element wherein the chromogen and the other reagents are previously incorporated into the prescribed layer.

4. Analytical element containing mordant: In the case that the coloring reagent forms an ionic dye, a mordant layer may be provided between the water-impermeable support and the reagent layer. The efficiency of optical detection can be improved by transferring the dye produced in proportion to the quantity of analyte in a sample to the mordant layer and trapping it there.

For example, in the case of forming a cationic dye by coloring reagents, a hydrophilic polymer layer containing a polymer having an anionic atom or atomic group bound to the polymer chain can be used as the mordant layer. In the case of forming an anionic dye by coloring reagents, a hydrophilic polymer layer containing a polymer having a cationic atom or atomic group bound to the polymer chain can be used.

The mordant polymers are described in detail in Japanese Patent KOKOKU No. 2-30466, U.S. Pat. Nos. 4,042,335, 4,166,093, 4,144,306, etc.

For example, anionic mordant polymers are alkali hydrolyzate of methyl vinyl ether-maleic anhydride copolymer, alkali metal salt or alkaline earth metal salt of polystyrene-p-sulfonic acid, alkali metal salt or alkaline earth metal salt of a copolymer of styrene-p-sulfonic acid and hydrophilic vinyl monomer, and the like disclosed at columns 13–14 of Japanese Patent KOKOKU No. 2-30466. The Japanese patent further discloses layers capable of incorporating the above polymers at columns 15–16.

5. Analytical element having a layer construction of the above 1–4 provided with light-shielding layer between hydrophilic polymer layer and spreading layer:

The light-shielding layer is a water-permeable layer where particulates having light-shielding ability or light-shielding ability and light-reflecting ability are dispersed in and supported by small amount of a hydrophilic polymer binder having film-forming ability. The light-shielding layer shields the color of an aqueous liquid sample, particularly red color of hemoglobin contained in a whole blood sample, when the detectable change (color change, coloring, etc.) is measured by reflection photometry from the light-transmissive support side, and also functions as a light-reflecting layer or a background layer.

Particulates having light-shielding ability and light-reflecting ability include titanium deoxide particulates (microcrystalline particulates having a particle size of about 0.1 μm to about 1.2 μm in rutile-type, anatase-type or brookite type, etc.), barium sulfate particulates, aluminum particulates and microflakes, and particulates having light-shielding ability include carbon black, gas black and carbon particulates. Among them, titanium dioxide particulates and barium sulfate particulates are preferred.

As the hydrophilic polymer binder having film-forming ability, there are the aforementioned hydrophilic polymers, and regenerated cellulose, cellulose acetate and the like which are weakly hydrophilic. Preferred ones are gelatin, gelatin derivatives, polyvinyl alcohol, polyacrylamide, maleic acid copolymers and the like. In the case of gelatin and gelatin derivatives, a known hardening agent (crosslinking agent) may be added.

6. Analytical element having a layer construction of the above 1–4 provided with water-impermeable gas-permeable layer (barrier layer) between hydrophilic polymer layer and spreading layer:

This analytical element is effective for the analysis of BUN (urea nitrogen) and CRE (creatinine) evolving ammonia gas, $CO_2$, etc. Either of whole blood and plasma can be used as samples. The barrier layer applicable to the invention includes the uniform coating layer of an uniform polymer disclosed in U.S. Pat. No. 4,066,403, membrane filter disclosed in U.S. Pat. No. 4,548,906 and the like.

The measuring reagent means the reagent which directly reacts with analyte which is the subject to be analyzed to produce a chemical change. That is, in the case that an enzyme is analyte, the measuring reagent is a substrate thereof, and in the case that analyte is an antigen (antibody), it is an antibody (antigen). In the case that analyte is a lipid, a sacharide or a metabolite and a detectable change is produced by an enzyme, the measuring reagent is the enzyme. In the case that the above reactions are induced by a general chemical reaction caused by a chemical reagent other than enzyme, it is the corresponding chemical substance. Examples are shown below:

In the case that analyte is GOT, the measuring reagent is aspartic acid and α-ketoglutaric acid, and in the case of amylase, it is starch having a high molecular weight or origosaccharide having a low molecular weight. In the case of GGT, it is L-γ-glutamylparanitro anilide, and in the case of ALP, it is paranitrophenyl phosphate. In the case of glucose, it is glucose oxidase, and in the case of uric acid, it is uricase. In the case of cholesterol, it is cholesterol esterase or cholesterol oxidase, in the case of neutral fats, it is lipase or esterase, in the case of urea, it is urease, etc. In the case that an indicator directly reacts with analyte, such as protein, albumin, Ca, inorganic phosphorus, etc. it is the indicator.

If a reaction reagent incorporated into the analytical element is unstable, such as some enzymes, the reaction reagent is preferably incorporated into the measuring reagent solution. That is, with respect to the distribution between the reagents to be incorporated into the measuring reagent solution and those to be incorporated into the analytical element, it may be varied using analytical performance and stock stability as an indicator. In the case of one analyte, the above distribution differs according to the construction of detecting reaction system.

Various reagents may be incorporated into the measuring reagent solution in order to adjust pH or ion strength so that reaction proceeds stably to obtain a good reproducibility, in order to improve diffusion and permeation into the materials constructing the analytical element, in order to improve the unstability of enzyme, etc. contained therein, or the like. Reagents for inhibiting reactions competitive to the detecting reaction may also be incorporated. As such a reagent, there are bilirubin oxidase, ascorbate oxidase, etc. Furthermore, a compound inhibiting an enzyme derived from a certain organism, such as an inhibitor of p-type amylase, may be added in order to detect an isozyme. In the case of measuring whole blood samples, $NaN_3$ or the like may be added which is effective as the inhibitor of catalase activity of hemoglobin.

In view of manufacturing, packaging, transportation, store, measuring operations, etc., the multilayer analytical element of the invention is preferably cut into square or circular pieces having a side or diameter of about 15 mm to about 30 mm, and put in a slide frame as disclosed in Japanese Patent KOKAI No. 57-63452, U.S. Pat. Nos. 4,169,751, 4,387,990, PCT application WO 83/00391, etc. for use. However, it may be formed into a stick similar to urine test paper, etc.

As the method of using the analytical element for whole blood, a prescribed amount of a whole blood sample is spotted onto the blood cell-separating layer, and waited until the plasma portion diffuses into the porous layer. The waiting time is usually 5 seconds to 1 minute. Then, the blood cell-separating layer is removed, and a fixed amount of measuring reagent solution is supplied to the porous layer where the plasma has been diffused. The supplied amount of the measuring reagent solution is set so that the diffused area of the measuring reagent solution becomes smaller than the diffuses area of the plasma, It is preferably set so that the diffused area of the measuring reagent solution is about 20 to 90%, preferably about 40 to 80%, and more preferably about 50 to 70% of that of the plasma. Both of the diffused area are at the layer to detect coloring. The measuring solution is spotted so as to diffuse within the diffused area of the plasma.

As mentioned heretofore, in the case of whole blood samples, the plasma amount moved into the porous layer arranged thereunder varies due to the difference of hematocrit value even the spotted amount is fixed. However, the influence by the variation can be omitted by limiting the amount of the measuring reagent solution as mentioned previously. After the removal of the blood cell-separating layer, the measurement may be conducted immediately, or the analytical element from which the blood cell-separating layer has been removed may be mailed to an assay organization and measured there. In the latter case, it is preferable that the analytical element without the blood cell-separating layer is dried and mailed under humidity controlled conditions so as not to be denatured. The method is disclosed in detail in Japanese Patent KOKAI No. 3-289543.

It is preferable to conduct the drying under substantially fixed conditions. Actually, it can be conducted according to disclosed in Japanese Patent KOKAI No. 3-289543 from page 25, line 9 to page 28, line 6, particularly from page 27, line 13 to page 28, line 6. For example, there is a method of heating the analytical element placed in an enclosure so that the circumference of the analytical element is covered. By employing this method, substantially constant dried state can be obtained without the influence of environmental temperature and moisture. A suitable temperature range is 30° to 45° C. A suitable temperature variation through the incubation is ±5° C., preferably ±3° C., more preferably ±1° C.

An incubator suitable for the above incubation which is carried out under substantially fixed conditions is disclosed in Japanese Utility Model KOKAI No. 3-126499. The incubator is composed that an analytical element (the analytical element portion of the invention from which the blood cell-separating layer is removed.) is placed in its receiving portion, heated by a heating means, and kept at a constant temperature. The incubator is provided with a detachable Cover which can seal the element-receiving portion at the upper part of the receiving portion, and the volume of the space formed in the element-receiving portion closed by the cover is designed so as to almost conform to the volume of the analytical element. Similar good reproducible results can be obtained by blowing dried air with a fixed temperature under substantially fixed conditions, but this method is disadvantageous because of expensiveness compared with the above incubator.

The inventors have further investigated as to the drying conditions, and found that it is preferable to conduct the drying of the analytical element portion in a closed container at lower than 50° C. in the presence of desiccant. Actually, the analytical element portion is sealed in a vinyl polymer bag with a fastener or a plastic container with a cap together with desiccant, and kept at room temperature or put in refrigerator or freezer. It is preferable to keep at lower than about 25° C. at least for 1 hour after spotting. The desiccant may be selected from known moisture absorbents which do not denature the analyte substantially, and zeolite and silica gel are preferred in view of safety and dehydrating ability, and zeolite is further preferable. Zeolite and silica gel can dry 4 to 10 sheets of the analytical element portion per 1 g. The desiccant may be formed into granules having a diameter of 1 to 3 mm, and put in a bag with good moisture permeability, such as made of Japanese paper or poly ester nonwoven fabric or nylon mesh bag.

Although the drying period varies according to the amount and kind of liquid sample, the amount and kind of desiccant, preferred conditions are capable of removing more than 90% of moisture content in the analytical element portion for about 1 to 10 hours, particularly about 1 to 3 hours. The drying period is influenced by temperature conditions. That is, the higher the storage temperature is, i.e. the higher the vaper pressure is, the shorter the drying period is. On the other hand, the analytical element portion can be dried by keeping once at a low temperature by leaving in a refrigerator or freezer and then rendering at more than 1° C. The low temperature drying is particularly effective in the case that the analyte is an enzyme because of inhibiting its denaturation.

The analytical element of the invention may be composed of the blood cell-separating layer and the spreading layer alone. In such a case, after plasma portion moves into the spreading layer, the blood cell-separating layer is peeled off. Then, the spreading layer is dried, and a constant area is cut off. The area is determined so as to obtain an amount of a sample necessary for the analysis of one analytical item, and the amount is 1 to 10 μl as the volume converted to liquid sample, as mentioned previously. A simple method of cutting a fixed area off is punching.

The extracting solvent which extracts the liquid sample contained in the cut piece is water, buffer solution, saline solution or the like. A reagent solution used for anlaysis may be used as the extracting solvent.

After the extraction, analysis may be conducted according to a known wet analysis of each analytical item. As the analytical reagent system, a known reagent system incorporated into dry analytical element may also be utilized, and the reagent system is usually preferable for the analytical method of the invention. The porous sheet after extraction is finished, is, in the case that it interferes measuring system, removed before measurement, but in the case that it does not interfere, it may be left.

Hereupon, "dried" is in the state that reactions substantially do not proceed or that degradation of analyte does not proceed. Therefore, it is different according to analyte, and for example, in the case of enzymes, moisture content in the hydrophilic polymer is less than 50%, preferably less than 20%, more preferably less than 10%.

In the analytical element for whole blood of the invention, by rendering the volume of the blood cell-separating layer smaller than the upper limit of the diffused volume of a whole blood sample to be spotted, the permiation of the plasma portion is led to the reverse side of the blood cell-separating layer, and to move into the porous layer is facilitated. By limiting the amount of the measuring reagent solution spotted after the plasma portion permeates into the porous layer, the diffused area of the measuring reagent solution is made constant. By rendering the diffused area of the measuring reagent solution smaller than that of the plasma portion, the colored area is made constant resulting in ensuring the quantitativeness.

According to the invention, the analytical error caused by scattering of hematocrit values is removed, and analysis can be conducted in a high accuracy.

EXAMPLES

EXAMPLE 1

(1) Preparation of Partial Analytical Element

Onto a transparent film base of polyethylene terephthalate 180 um in thickness provided with undercoating, polyvinyl alcohol ("KL 506", Kuraray) containing 0.2% of nonionic surfactant p-nonylphenoxypolyglycidol (containing 10 glycidol unit on average) and an epoxy compound ("ARALDITE DY 022", Ciba-Geigy) as crosslinking agent was applied so that the dry thickness was about 15 μm, and dried. Polyester knitted fabric which was made hydrophilic was laminated thereonto according to the method disclosed in Japanese Patent KOKAI No. 62-224299. 1.5% hydroxyethyl cellulose ("HPC", Shin-Etsu Chemical) ethanol solution containing 0.25% of nonionic surfactant ("HS 240", Nippon Oil and Fats) was applied thereonto so that the coating amount was 250 g/m$^2$.

(2) Preparation of Blood Cell-Separating Layer Portion

A polytetrafluoroethylene microporous membrane of which the surface and the inner surface of the pores were made hydrophilic by hydrophilic polymer ("POREFLON WPW-100-100", Sumitomo Denko) was punched into disc having a diameter of 12 mm. Separately, a glass fiber filter paper ("CA-55", Advantec) was punched into disc having a diameter of 8 mm. A single face adhesive tape made of plastic was punched into disc 15 mm in diameter having a circular hole 6 mm in diameter at the center, and the above microporous membrane disc and glass fiber filter disc were adhered thereonto so that the glass fiber filter disc is positioned on the side near the adhesive tape.

(3) Assembly of Analytical Element for Whole Blood

The partial analytical element prepared in the above item (1) was punched into, square having a size of 15 mm×15 mm, and incorporated into a plastic mount made of high impact polystyrene 28 mm in longitudinal×24 mm in lateral×1.5 mm in thickness having a circular hole 10 mm in diameter at the center to prepare an analytical element portion having the same form as disclosed in Japanese Patent KOKAI No. 57-63452. The blood cell-separating layer portion prepared in the above item (2) was adhered to fix onto the upper face of the above analytical element portion so that both centers are in accord with each other wherein the spreading layer of the anlaytical element portion faced the microporous membrane of the blood cell-separating layer portion, and thus, the analytical element for whole blood was completed.

(4) Preparation of Measuring Reagent Solution for Total Protein

The following reagent composition was dissolved into 20 ml of water to prepare a measuring reagent solution utilizing Biuret reaction.

| | |
|---|---|
| Copper sulfate (5 hydrates) | 3.5 g |
| Tartaric acid | 2.3 g |
| Lithium hydroxide | 3.8 g |
| Cetylmethyl ammonium bromide | 0.1 g |

(5) Preparation of Samples

A whole blood sample drawn from a healthy person with heparin was divided into 3 test tubes in an amount of each 2 ml, and to No. 2 and No. 3 test tubes, a small amount of bovine serum albumin to prepare whole blood samples. Each part of them was centrifuged, and total protein concentration of the plasma protion obtained was measured using an analyzer ("HITACHI 7050", Hitach).

Separately, 10 ml of the above whole blood was centrifuged at 3,000 rpm for 2 minutes to separate into a whole blood portion having a high hematocrit value and a plasma poriton. The hematocrit (Hct) value of the whole blood portion was measured and found to be 68%. Samples Nos. 4–7 were prepared with varying the volume ratio of the whole blood portion to the plasma portion. The Hct value of each sample was 18%, 39%, 48% and 62%.

(6) Spotting of Samples

Each 30 μl of the above whole blood samples was spotted onto the analytical element for whole blood prepared in the above item (3). The whole blood was first stood up in a form of drop on the glass fiber filter paper and then permeated into the under side layers. After leaving for one minute from the spotting, an end of the adhesive tape was pinched by a pincette, and the blood cell-separating layer portion was separated to remove from the analytical element portion placed in the plastic mount. It was confirmed that only the plasma was diffused into the spreading layer in a circle about 8–15 mm in diameter by visual observation. According as the hematocrit value increased, the transferred amount of the plasma was reduced.

(7) Dehydration of Separated Plasma

The analytical element portion containing the transferred plasma obtained in the item (6) dried by putting in an aluminum heating block heated at 37° C. and leaving for 5 minutes, according to the method described in Japanese Patent KOKAI No. 3-289543.

(8) Measurement of Total Protein

The analytical element portions obtained in the above item (7) were set in "Fuji Dry Chem 5500" analyzer (Fuji Photo Film Co., Ltd.). 5 μl of the measuring reagent solution prepared in (4) was sucked into a pipetting device, and spotted. Each analytical element portion was incubated for 6 minutes, and then, reflection optical density was measured at the wave length of 540 mn, according to conventional manners. The colored circle corresponding to the diffusion of the measuring reagent solution had almost the constant diameter of about 7 mm.

(9) Preparation of Calibration Curve

Figure 1:
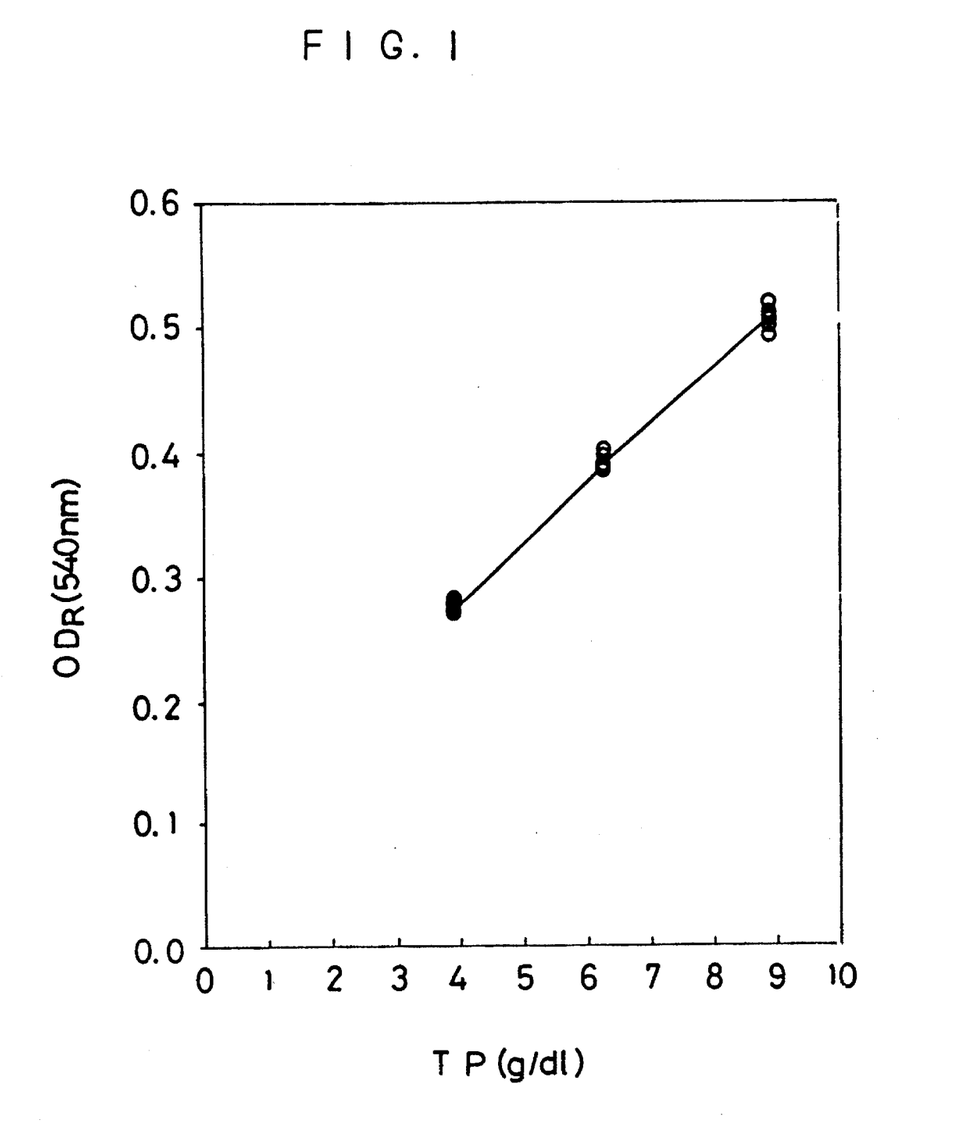
FIG. 1 is a graph of a calibration curve between total protein concentration and reflection optical density.

A calibration curve shown in FIG. 1 was obtained indicating the relationship between the relfection optical densities obtained in (8) and the measured values of HITACHI 7050 as to the samples Nos. 1–3.

(10) Measured Value of Samples Different in Hematocrit Value

Using the samples Nos. 4–7 prepared in the above (5), the measuring operations of (6)–(8) repeated three times, and each protein concentration was determined by using the calibration curve obtained in (9) as follows:

| Sample | No. 4 | No. 5 | No. 6 | No. 7 |
|---|---|---|---|---|
| Hct Value (%) | 18 | 39 | 48 | 63 |
| Measured Value (mg/dl) | 8.8 | 8.5 | 7.8 | 6.7 |

EXAMPLE 2

(1) Prepartion of Partial Analytical Element

A partial analytical element was prepared according to the item (1) of Example 1, except that polyvinyl alcohol coating solution was replaced by a gelatin coating solution containing 800 mg/m$^2$ of 2-(3,5-dimethoxy-4-hydroxyphenyl)-4-[4-(dimethylamino)phenyl]-5-phenethylimidazole and 12,000 mg/m$^2$ of Triton X-100 (trade name). The solution for spreading control similar to item (1) of Example 1 was applied onto the spreading layer and then dried to prepare the partial analytical element.

(2) Preparation of Analytical Element for Whole Blood

An analytical element for whole blood was prepared similar to items (2) and (3) of Example 1.

(3) Preparation of Measuring Reagent Solution for GPT

The measuring reagent solution having the following composition was prepared.

| L-alanine | 620 mg |
| α-ketoglutaric acid.2Na salt | 93 mg |
| 20% magnesium chloride | 275 mg |
| Peroxidase | 3416 U |
| Cocarboxylase | 21 mg |
| Flavin adnine dinucleotide | 5 mg |
| Pyruvate oxidase | 3088 U |
| 10 mM tris (pH 7.5) | 10 ml |

(4) Perparation of Samples

Whole blood samples Nos. 1–7 different in GPT activity or hematocrit value were prepared similar to the item (5) of Example 1.

(5) Measurement of GPT Activity

Using the above samples, the measuring operations of (6)–(8) of Example 1 were conducted to measure GPT activity. In the process of the item (8), the measured wave length was 640 nm, and the measuring period was 5 minutes and the GPT activity was calculated using 5 minute value-1 minute value.

(6) Preparation of Calibration Curve and Influence of Hematocrit Value

The relationship between the measured value of the invention and the hematocrit value of whole blood samples was investigated similar to the (9) and (10) of Example 1, and the results shown in the following table.

| Sample | No. 4 | No. 5 | No. 6 | No. 7 |
|---|---|---|---|---|
| Hct (%) | 21 | 38 | 51 | 63 |
| GPT Activity (U/l) | 23 | 21 | 20 | 13 |

According to the results, it was confirmed that almost constant values of GPT activity can be obtained in a wide renge of hematocrit value except a particularly high hematocrit value range of more than 60%.

EXAMPLE 3

(1) Preparation of Partial Analytical Element

Onto a colorless transparent flat sheet of polyethylene terephthalate (PET) 180 μm in thickness provided with gelatin undercoating, a water absorption layer having the following composition was applied so that the dry thickness was 15 μm, and dried.

| Deionized gelatin | 20 g |
| p-nonylphenoxypolyglycidol (containing 10 glycidol unit on average) | 1.5 g |

Bis [(vinylsulfonylmethylcarbonyl)amino]methane 220 mg

Subsequently, an adhesive layer having the following composition was applied in an aqueous solution so that the dry thickness was 1 μm onto the water absorption layer, and dried.

| Deionized gelatin | 4.0 g |
| p-nonylphenoxypolyglycidol (containing 10 glycidol unit on average) | 430 mg |

The whole surface of the adhesive layer was moistened almost nuiformly by supplying water at a rate of about 30 g/m$^2$, and a broad woven fabric made of PET having a thickness of about 150 μm and a void volume of 9.8 μl/m$^2$ was laminated thereonto with light pressing, and then dried.

The following aqueous solution was applied onto the fabric almost uniformly at a rate of 100 ml/m$^2$ and dried to complete the partial analytical element.

| Hydroxypropylmethyl cellulose (containing 28–30% of methoxy group and 7–12% of hydroxypropyl group, solution viscosity of 50 cps at 2% aqueous solution at 20° C.) | 8.7 g |
| Octylphenoxypolyethyoxyethanol (containing 10 hydroxyethylene unit on average) | 27 g |
| Water | 964.3 g |

(2) Preparation of Blood Cell-Separating Layer Portion

A tricot knitted fabric about 250 μm in thickness formed by knitting 50 denier PET spun yarn with 36 gauge was impregnated with the following aqueous solution, and dried.

| Polyethylene glycol (mean molecular weight: 50,000) | 2.0 g |
| Sodium tetraborate | 2.0 g |
| Water | 96 g |

The above tricot fabric was heated to 80° C., and a hot melt adhesive ("H 950" Nitta Gelatin) melted at 130° C. was adhered in dots on the surface by transferring from gravure roll in the gravure roll in the gravure printing process. The dot pattern of the gravure roll was formed of circular dots 0.3 mm in diameter having intervals of 0.6 mm as the distance between the center of dots and an areal ratio of dots of about 20%. The adhered amount of the adhesive was about 2 g/m$^2$. The non-glossy surface of cellulose acetate membrane filter having an effective pore size of 3.0 μm, a thickness of 140 μm and a void content of about 80% was faced to the surface of the tricot fabric at a high temperature immediately after the transferring the adhesive, and they were passed between laminating rollers. Thus, they were integrated by partial adhesion to complete the blood cell-separating layer portion. The same adhesive was also adhered in dots onto the other side of the membrane filter by the same method, and then cooled naturally.

(3) Assembly of Analytical Element for Whole Blood

The blood cell-separating layer portion thus obtained was punched into circle 8 mm in diameter, and adhered to the partial analytical element portion by heating at 60° C. for 2 minutes with pressing at 2 kg/cm$^2$ to complete the multilayer analytical element for whole blood.

The analytical element was cut into square having a side of 15 mm, and placed in a plastic mount disclosed in Japanese Patent KOKAI No. 57-63452 which is measurable by an analyzer ("Fuji Dry Chem. 5500", Fuji Photo Film Co., Ltd.)

(4) Preparation of Samples and Spotting

Samples were prepared and spotted onto the above analytical element similar to Example 1.

(5) Dehydration

The partial analytical element was put in a moistureproof small bag 5 cm×7 cm in size made of a laminate composed of polyethylene and aluminum foil together with 2 g of granular zeolite (Shin-Ethu Kasei Kogyo) having a particle size of about 1 mm placed in a moisture-permeable bag made of polyester nonwoven fabric, sealed and kept for 3 hours at room temperature.

(6) Preparation of Measuring Reagent Solution

The same measuring reagent solution as Example 1 was prepared.

(7) Spotting of Measuring Reagent Solution and Measurement

Similar to Example 2, 3 µl of the measuring reagent solution was spotted, and measured using Fuji Dry Chem. 5500 analyzer. The results are shown in the following table.

| Sample | No. 4 | No. 5 | No. 6 | No. 7 |
|---|---|---|---|---|
| Hct (%) | 17 | 35 | 47 | 59 |
| GPT Activity (U/l) | 27 | 29 | 26 | 24 |

We claim:

1. In an analytical element for use in the analysis of a whole blood sample, the element comprising the following layers laminated in this order:

a blood cell-separating layer, a porous layer, a hydrophilic polymer layer, and a water-impermeable support, the improvement which comprises, the hydrophilic polymer layer further comprising a fluorine containing microporous membrane, the blood cell-separating layer having a volume less than the maximum diffused volume of a whole blood sample having a hematocrit value of 70%, having a pore size of 1 to 20 µm, avoid content of 50 to 95% and a layer thickness of 10 to 200 µm.

2. The analytical element of claim 1 wherein the fluorine-containing polymer is polytetrafluoroethylene.

3. The analytical element of claim 1 wherein the fluorine-containing polymer microporous membrane is rendered hydrophilic by coating with a surfactant or a hydrophilic polymer.

4. The analytical element of claim 1 wherein the cell-separating layer further comprises a glass fiber filter paper adhered to the membrane layer on the side from which the sample is spotted.

5. In an analytical element for use in the analysis of a whole blood sample, the element comprising the following layers laminated in this order:

a blood cell-separating layer, a porous layer, a hydrophilic polymer layer, and a water-impermeable support, the improvement which comprises, the blood cell-separating layer having a volume less than the maximum diffused volume of a whole blood sample having a hematocrit value of 70%, wherein the blood cell-separating layer comprises a fluorine-containing polymer microporous membrane layer rendered hydrophilic.

6. The analytical element of claim 5 wherein the fluorine-containing polymer microporous membrane layer rendered hydrophilic 7. The analytical element of claim 5 wherein the fluorine-containing is polytetrafluoroethylene.

8. The analytical element of claim 5 wherein the fluorine-containing polymer microporous membrane is rendered hydrophilic by coating with a surfactant or a hydrophilic polymer.

9. The analytical element of claim 5 wherein the cell-separating layer further comprises a glass fiber filter paper adhered to the membrane layer on the side from which the sample is spotted.

* * * * *